US00PP11098P

United States Patent [19]

Walden

[11] Patent Number: Plant 11,098

[45] Date of Patent: Oct. 19, 1999

[54] FLORIBUNDA ROSE PLANT NAMED 'JACPRICL'

[75] Inventor: John K. Walden, Thousand Oaks, Calif.

[73] Assignee: Bear Creek Gardens, Inc., Medford, Oreg.

[21] Appl. No.: 08/998,962

[22] Filed: Dec. 29, 1997

[51] Int. Cl.[6] ..... A01H 5/00

[52] U.S. Cl. ..... Plt./145

[58] Field of Search ..... Plt./144, 145

*Primary Examiner*—Howard J. Locker

*Attorney, Agent, or Firm*—Klarquist Sparkman Campbell Leigh & Whinston, LLP

[57] ABSTRACT

Floribunda rose plant having pale yellow flower color, damask fragrance, long shelf life, excellent plant habit for both pot and landscape culture, disease resistance to powdery mildew, and thick firm petals.

1 Drawing Sheet

The present invention relates to a new and distinct variety of rose plant of the floribunda class which was originated by me crossing the variety 'JACimin', (U.S. Plant Pat. No. 8,850), with the variety 'INTERprince', (U.S. Plant Pat. No. 8,102).

The primary objective of this breeding was to produce a new rose variety having the plant (full and round), color, disease resistance, foliage, and flower form of the female parent combined with the clustering of flowers, petal substance and flower longevity of the male parent.

This objective was substantially achieved, along with other desirable improvements, as evidenced by the following unique combination of characteristics that are outstanding in the new variety and that distinguish it from its parents, as well as from all other varieties of which I am aware:

1. Excellent petal substance, i.e., petals are thick and firm;
2. Excellent plant habit both as a pot rose and landscape plants;
3. Bright, healthy foliage, resistant to powdery mildew;
4. Fragrance of damask roses;
5. Very good clustering of blooms; and
6. Long shelf-life of sixeen to nineteen days.

Asexual reproduction of this new variety by cutting propagation, as performed at Waco and Somis, Calif., shows that the foregoing and all other characteristics and distinctions come true to form and are established and transmitted through succeeding propagations.

The accompany illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACimin' (U.S. Plant Pat. No. 8,850).

*Pollen parent.*—'INTERprince' (U.S. Plant Pat. No. 8,102).

Classification:

*Botanical.*—*Rosa hybrida.*

*Commercial.*—Floribunda rose.

FLOWER

Observations made from specimens grown in garden and greenhouse environments at Somis, Calif. from October, 1994 to September, 1997.

Blooming habit: Continuous.

Bud:

*Size.*—Three quarters inch when the petals start to unfurl.

*Form.*—The bud form is short, pointed ovoid.

*Color.*—When sepals first divide, bud colro is Yellow-orange Group 18D with a blush on petal tips of Red Group 36C. When half blown, the upper sides of the petals are Yellow Group 4D; and the lower sides of the petals are Yellow Group 4D.

*Sepals.*—Color: Yellow-green Group 144A. Surface texture: Smooth to slightly rough. There are three lightly appendaged glandular serrated sepals. There are two unappendaged sepals with hairy edges.

*Receptacle.*—Color: Green Group 143C. Shape: Funnel. Size: Small (¼"×5⁄16"). Surface: Smooth, very finely hairy.

*Peduncle.*—Length: Medium (1⁵⁄₁₈"–1⅞"). Surface: Glandular. Color: Light green (Green Group 143C). Strength: Stiff, erect.

*Opening.*—Buds open slowly in a spiraled to imbricated fashion.

Bloom:

*Size.*—Medium. Average open size is two and one-half to three inches.

*Borne.*—Singly, and occasionally in clusters of three buds.

*Stems.*—Short (8 to 12 inches), strong.

*Form.*—When first open: High-centered. Permanence: All petals curl, quill fashion.

*Petalage.*—Number of petals under normal conditions: 45–50.

*Color.*—The upper sides of the petals are Yellow Group 11D. The reverse sides of the petals are Yellow Group 11D. The base of each petal is Yellow Group 4C. The major color on the upper side is Yellow Group 11D.

*Variegations.*—None.

*Discoloration.*—At the end of the first day: Yellow-orange Group 18C toward the center of the flower, lightening to Yellow Group 11D. At the end of the third day: Yellow Group 4D being a creamy, warm white to very pale yellow.

*Fragrance.*—Moderate damask scent.

Petals:

*Texture.*—Thick, leathery.

*Shape.*—Pointed, deltoid.

*Form.*—Tips slightly recurved to moderately quilled.
*Arrangement.*—Imbricated. Petaloids in the center are few.
*Persistence.*—Hang on and dry.
*Lastingness.*—On the plant: Very long (16–19 days). As a cut flower: Long (14–16 days).

Reproductive parts:
*Anthers.*—Size: Medium. Quantity: Many. Color: Yellow. Arrangement: Regular around styles.
*Filaments.*—Color: Yellow.
*Pollen.*—Color: Lemon yellow.
*Styles.*—Color: Red Group 47B.
*Stigmas.*—Color: White.

Plant:
*Form.*—Bush. In a pot a mature plant is about 16 to 18 inches in height and 18 inches in width. In a garden a mature plant will be 24 to 30 inches in height and 30 to 36 inches in width.
*Growth.*—Vigorous; upright; branching; and spreading.

Foliage: Number of leaflets on normal mid-stem leaves: Seven.
*Size.*—Large (5" long×3¾" wide).
*Quantity.*—Normal.
*Color.*—New foliage: Upper and lower surfaces: Greyed-red Group 181A. Old Foliage: Upper surface: Green Group 137A. Lower surface: Green Group 137C.
*Shape.*—Broadly oval.
*Texture.*—Upper side: Glossy, smooth.
*Edge.*—Serrated.
*Serration.*—Double, large.
*Petiole rachis.*—Color: Reddish changing rapidly to green.
*Petiole underside.*—With prickles.
*Stipules.*—Medium, serrated.
*Disease resistance.*—Resistant to mildew under normal growing conditions in the greenhouse at Somis, Calif.

Wood:
*New wood.*—Color: Medium green (Yellow-green Group 146C). Bark: Smooth.
*Old wood.*—Color: Green (Yellow-green Group 146B). Bark: Smooth.

Prickles:
*Quantity.*—On main canes from base: Few. On laterals from main canes: Few.
*Form.*—Medium (¼" to 5/16") in length, straight.
*Color when young.*—Greyed-Red 178B; turning to between Greyed-Yellow 160C and 160D as they mature.

Small prickles:
*Quantity.*—On main stalks: None. On laterals: None.

I claim:

1. A new and distinct variety of rose plant of the floribunda class substantially as herein shown and described, characterized particularly as to novelty by its pale yellow flower color, damask fragrance, long shelf-life, excellent plant habit for both pot and landscape culture, disease resistance to powdery mildew, and thick, firm petals.

* * * * *

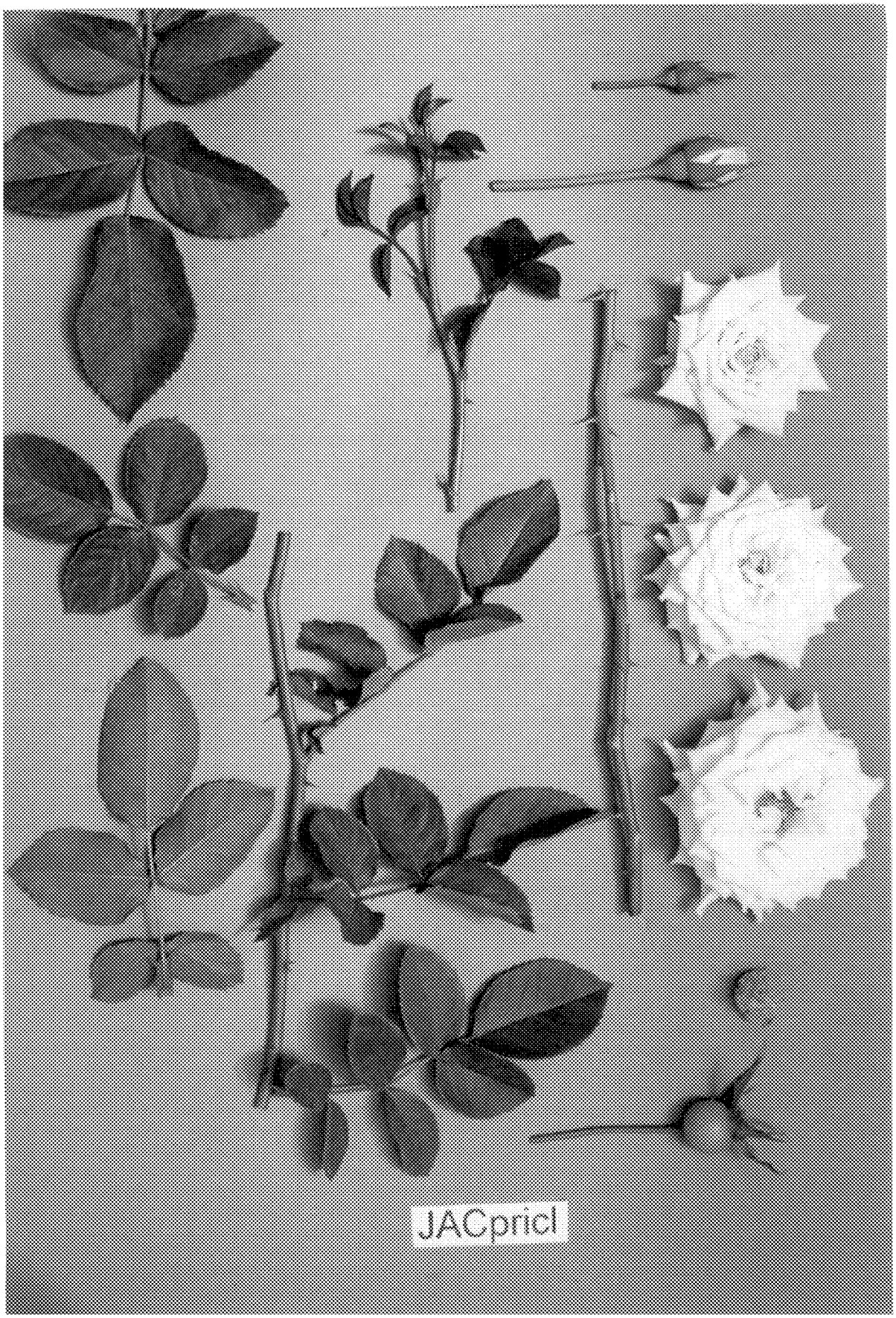
JACpricl

UNITED STATES PATENT AND TRADEMARK OFFICE

CERTIFICATE OF CORRECTION

PATENT NO. : PP11,098
DATED : October 19, 1999
INVENTOR(S) : John K. Walden

It is certified that error appears in the above-identified patent and that said Letters Patent is hereby corrected as shown below:

In the Specification:

Column 1,
Line 6, reads "plant (full". It should read -- plant habit (full --.
Line 21, reads "sixeen". It should read -- sixteen --.
Line 23, reads "Waco". It should read -- Wasco --.

Column 2,
Line 7, reads "colro". It should read -- color --.
Line 19, reads "1 5/18". It should read -- 1 5/8 --.

Signed and Sealed this

Tenth Day of July, 2001

*Attest:*

Nicholas P. Godici

*Attesting Officer*

NICHOLAS P. GODICI
*Acting Director of the United States Patent and Trademark Office*